United States Patent
Zhang et al.

(10) Patent No.: US 10,667,479 B2
(45) Date of Patent: Jun. 2, 2020

(54) MOLECULAR BREEDING METHOD FOR IMPROVING COTTON FIBER STRENGTH BY USING CHR.7 SINGLE QTL SEGMENT SUBSTITUTION LINE

(71) Applicant: Cotton Research Center of Shandong Academy of Agricultural Sciences, Jinan (CN)

(72) Inventors: Jun Zhang, Jinan (CN); Yu Chen, Jinan (CN); Furong Wang, Jinan (CN); Chuanyun Zhang, Jinan (CN); Guodong Liu, Jinan (CN); Jingxia Zhang, Jinan (CN); Zhaohai Du, Jinan (CN)

(73) Assignee: Cotton Research Center of Shandong Academy of Agricultural Sciences, Jinan (CN)

( * ) Notice: Subject to any disclaimer, the term of this patent is extended or adjusted under 35 U.S.C. 154(b) by 0 days.

(21) Appl. No.: 16/043,404

(22) Filed: Jul. 24, 2018

(65) Prior Publication Data

US 2019/0223398 A1    Jul. 25, 2019

(30) Foreign Application Priority Data

Jan. 24, 2018 (CN) .......................... 2018 1 0069639

(51) Int. Cl.
  A01H 5/10 (2018.01)
  A01H 6/60 (2018.01)
  A01H 1/04 (2006.01)

(52) U.S. Cl.
  CPC ............... *A01H 1/04* (2013.01); *A01H 6/604* (2018.05)

(58) Field of Classification Search
  None
  See application file for complete search history.

(56) References Cited

FOREIGN PATENT DOCUMENTS

CN    102181442    * 9/2011

OTHER PUBLICATIONS

Fang et al., 2017, Fine-mapping qFS07.1 controlling fiber strength in upland cotton (*Gossypium hirsutum* L.), Theor. Appl. Genet. 130: 795-806.*

Wang et al., 2013, Genetic dissection of the introgressive genomic components from *Gossypium barbadense* L. that contribute to improved fiber quality in *Gossypium hirsutum* L., Molecular Breeding 32: 547-562.*

Xiao et al., 2009, New SSR Markers for Use in Cotton (*Gossypium* spp.) Improvement, The Journal of Cotton Science 13: 75-157.*

GQ394655—*Gossypiunn hirsutum* clone MONCS1678 SSR marker, published Aug. 25, 2009.*

K0229374—GH_TBh002J19r *Gossypium hirsutum* genomic sequence, published Dec. 5, 2014.*

Liu, Xia, et al., "*Gossypium barbadense* genome sequence provides insight into the evolution of extra-long staple fibe and specialized metabolites," Scientific Reports, Nature.com, Sep. 2015, pp. 1-14, vol. 5:14139 | DOI: 10.1038/srep14139 (14 pages).

Wang, Furong, et. al., "Genetic dissection of the introgressive genomic components from *Gossypium barbadense*L. that contribute to improved fiber quality in *Gossypium hirsutum* L.," Molecular Breeding, New Strategies in Plant Improvement, Jul. 2013, published online DOI 10.1007/s11032-013-9888-y (18 pages).

Yuan, Daojun, et. al., "The genome sequence of Sea-Island cotton (*Gossypium barbadense*) provides insights into the allopolyploidization and development of superior spinnable fibres," Scientific Reports, Nature.com, Dec. 2015, pp. 1-16, vol. 5:17662 | DOI: 10.1038/srep17662 (16 pages).

Zhang, Tianzhen, et. al., "Sequencing of allotetraploid cotton (*Gossypium hirsutum* L. acc.. TM-1) provides a resource for fiber improvement," Nature Biotechnology, Advance Online Publication, Apr. 2015, doi:10.1038/nbt.3207 (10 pages).

* cited by examiner

Primary Examiner — Bratislav Stankovic
(74) Attorney, Agent, or Firm — Wood Herron & Evans LLP

(57) ABSTRACT

A cotton molecular breeding method includes (1) obtaining a chr.7 single QTL segment substitution line with high fiber strength, and (2) using the obtained chr.7 single QTL segment substitution line as a non-recurrent parent (♂) to cross with a recurrent parent (♀) to obtain an F1 generation. Then (3) the $F_1$ generation is back-crossed with the recurrent parent to obtain a $BC_1F_1$ generation, and (4) plants of the $BC_1F_1$ generation are screened for plants carrying the chr.7 single QTL segment, and then the screened plants are back-crossed with the recurrent parent for 2-4 times to obtain a $BC_nF_1$ generation. The method also includes (5) screening plants of the $BC_nF_1$ generation for plants carrying the chr.7 single QTL segment, and selfing the screened plants for 1-3 times to obtain a bred line $BC_nF_m$ having the high cotton fiber strength.

4 Claims, 1 Drawing Sheet
Specification includes a Sequence Listing.

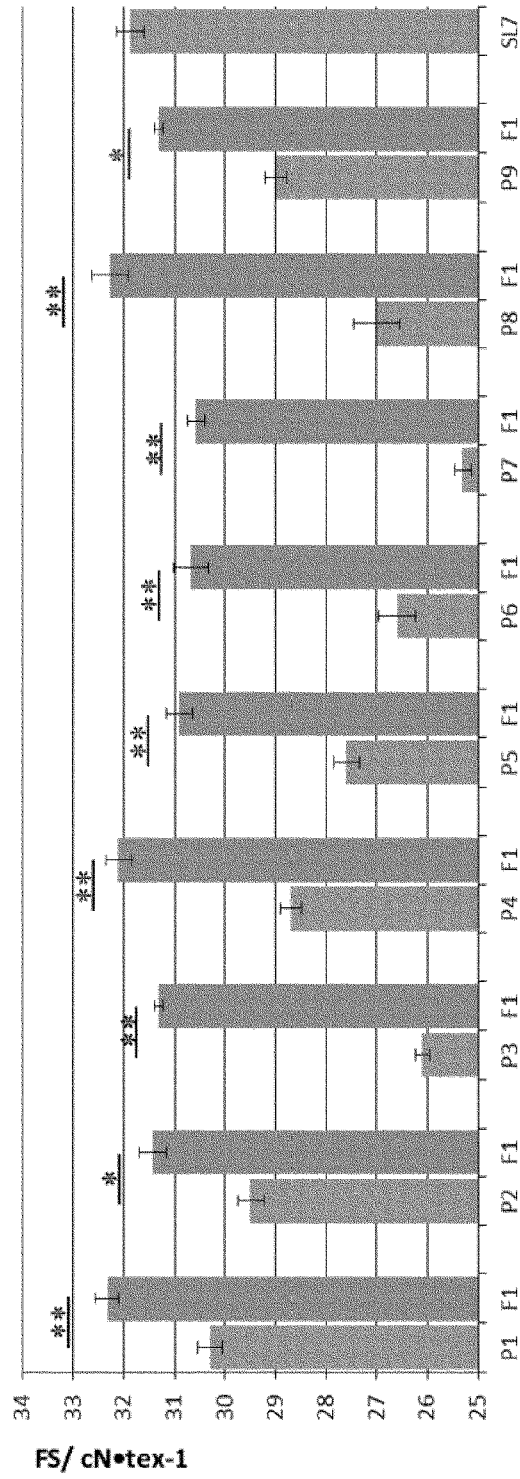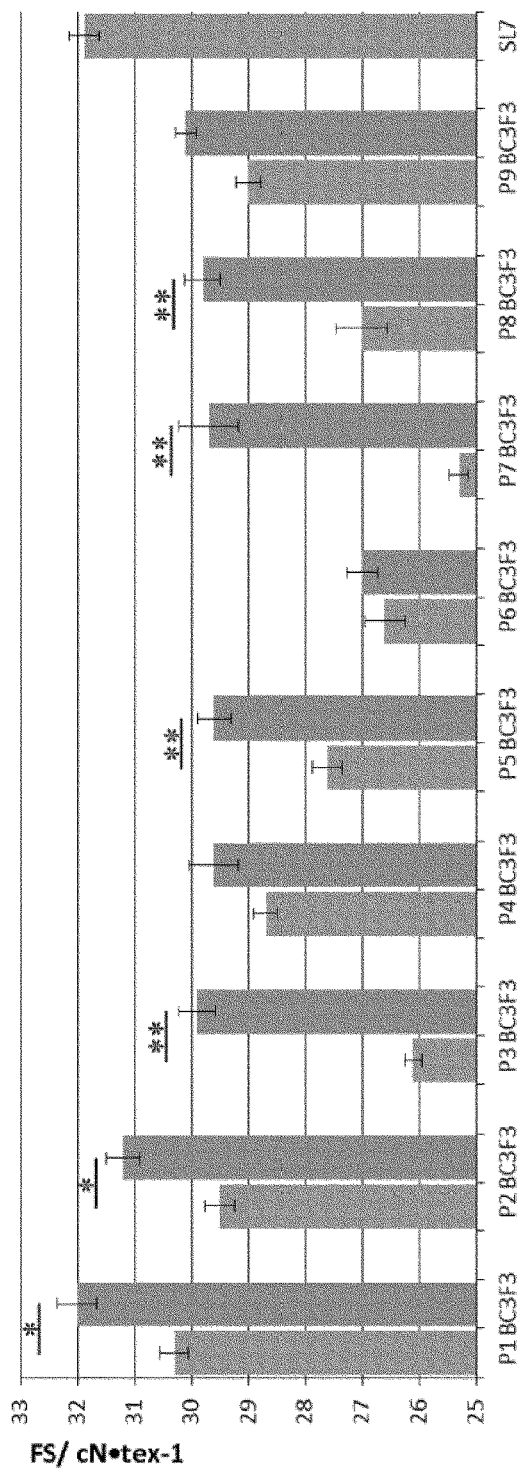

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gttccaaatc aatctcgtgt                                                 20

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ggctgttaca gatcaaactc cc                                              22

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
```

```
ccctacaaca gtttgatacc atga                                              24

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
attgagggta ttgctataca tcgg                                              24

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
aaaatactaa agtcgataga attgc                                             25

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
accgttccaa atagggtc                                                     18
```

MOLECULAR BREEDING METHOD FOR IMPROVING COTTON FIBER STRENGTH BY USING CHR.7 SINGLE QTL SEGMENT SUBSTITUTION LINE

CROSS-REFERENCE TO RELATED APPLICATION

This application claims priority to Chinese application number 201810069639.3, filed Jan. 24, 2018. The above-mentioned patent application is incorporated herein by reference in its entirety.

TECHNICAL FIELD

The present invention pertains to cotton molecular breeding, and, in particular, relates to a molecular breeding method for improving cotton fiber strength by using a chr.7 single QTL Segment substitution line.

BACKGROUND

Cotton is an important economic crop and is a main raw material in textile industry. For a long period, yield and quality of cotton fiber have always been two important goals of cotton breeding improvement. Upland cotton (*Gossypium hirsutum* L.) accounts for about 90% of the world's current total cotton production due to its high yield and wide adaptability (Zhang et al. 2015: Sequencing of allotetraploid cotton (*Gossypium hirsutum* L. acc. TM-1) provides a resource for fiber improvement. Nat Biotechnol 33:531-537). However, since the fiber quality of the upland cotton is still not ideal enough to meet the requirements of rapid development of modern textile technology, while the genome of Sea-Island cotton (*G. barbadense* L) contains excellent fiber genes (Liu et al. 2015: *Gossypium barbadense* genome sequence provides insight into the evolution of extra-long staple fiber and specialized metabolites. Sci Rep 5:14139; Wang et al. 2013: Genetic dissection of the introgressive genomic components from *Gossypium barbadense* L. that contribute to improved fiber quality in *Gossypium hirsutum* L. Molecular Breeding 32:547-562; Yuan et al. 2015: The genome sequence of Sea-Island cotton (*Gossypium barbadense*) provides insights into the allopolyploidization and development of superior spinnable fibres. Sci Rep 5:17662), it has always been a goal pursued by breeders how to introduce the excellent genes into the upland cotton which has high yield and wide adaptability, to improve the fiber quality of the upland cotton. However, due to reproductive isolation existed in interspecific crossing or severe segregation distortion in cross offspring, it is very difficult to directly use these excellent genetic resources for breeding, which is also an important reason why the improvement of upland cotton fiber quality has always been stagnant.

Accordingly, it would be desirable to improve cotton molecular breeding methods to address these and other drawbacks in the known art.

SUMMARY

An objective of the present invention is to provide a rapid and efficient molecular breeding method for improving cotton fiber strength by using a chr.7 single QTL segment substitution line.

To this end, a molecular breeding method is provided in one embodiment for improving the cotton fiber strength by using a chr.7 single QTL chromosomal segment substitution line. The method includes the steps of: (1) using Lumianyan 22 as a female parent and Luyuan 343 as a male parent to construct a recombinant inbred line (RIL) $F_8$, utilizing this population to detect one major-effect QTL associated with fiber strength on a chr.7 chromosome, selecting an individual plant carrying the target chr.7 single QTL segment to continuously back cross with the Lumianyan 22 for 3-5 times, and using an SSR molecular marker to screen back-crossed offsprings for obtaining a chr.7 single QTL segment substitution line with high fiber strength; (2) using the chr.7 single QTL segment substitution line obtained in step (1) as a non-recurrent parent to cross with a recurrent parent to obtain an $F_1$ generation, the recurrent parent being a parent having a fiber quality to be improved; (3) back crossing the $F_1$ generation obtained in step (2) with the recurrent parent to obtain a $BC_1F_1$ generation; (4) using the SSR molecular marker to screen plants of the $BC_1F_1$ generation for plants carrying the target chr.7 single QTL segment, and back crossing the screened plants with the recurrent parent for 2-4 times to obtain a $BC_nF_1$ generation; and (5) using the SSR molecular marker to screen plants of the $BC_nF_1$ generation for plants carrying the target chr.7 single QTL segment, and selfing the screened plants for 1-3 times to obtain a bred line $BC_nF_m$ having high cotton fiber strength. The primer pair used for SSR molecular marker screening includes a DPL0852 primer pair, a DPL0757 primer pair, and a DC40182 primer pair; and the sequences are Seq ID Nos. 1-6, respectively.

In one aspect, the chr.7 single QTL segment substitution line has fiber length of 30-31.1 mm and fiber strength of 31-33.3 cN/tex.

In another aspect, for the 1-3 times selfing performed in step (5), the SSR molecular marker is used after each time of selfing to screen out a plant carrying the chr.7 single QTL segment for the next selfing.

In a further aspect, the recurrent parent described in step (2) is Lumianyan 29, Lu 7619, Lu 6269, Ji 958, Lumianyan 36, Lumianyan 37, Lu 53586, Lumian 301, or Lumian 319. For example, the number of times of back-cross in step (4) is 3.

In an exemplary embodiment, the number of times of selfing in step (5) is 2.

Compared with the prior art, the method described herein achieves several advantages and beneficial effects. These include by using the chr.7 single QTL segment substitution line provided by the present invention uses the chr.7 single QTL segment substitution line having the high cotton fiber strength to cross and back-cross with the recurrent parent and to selfing, and by adopting the chr.7 single QTL segment substitution line having the high cotton fiber strength, it can stably substitute the chr.7 single QTL segment having the high cotton fiber strength into the recurrent parent, without substituting a gene other than the chr.7 single QTL segment substitution line having the high cotton fiber strength into the recurrent parent, thereby allowing the recurrent parent to have an excellent fiber strength trait. At the same time, by using the SSR molecular marker during the breeding process to assist screening of a plant having a target trait, the method can quickly and efficiently cultivate a new cotton line with excellent fiber quality in 2-3 years. The methods of the present invention therefore provide numerous advantages and technical effects that improve cotton molecular breeding.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrates one or more embodiments of the invention and, together with the general description given above and the detailed description given below, explains the one or more embodiments of the invention.

FIG. 1 shows a graphical plot illustrating an evaluation of the effect of fiber strength in different genetic backgrounds of the $F_1$ generation in a first embodiment of the invention.

FIG. 2 shows a graphical plot illustrating an evaluation of the effect of fiber strength in different genetic backgrounds of the $BC_3F_3$ generation in the first embodiment of the invention.

DETAILED DESCRIPTION

Embodiments of the invention are illustrated below with reference to the accompanying drawings. The preferred embodiments described here are used only to describe and explain the present disclosure, but not to limit the present disclosure.

The present invention provides a molecular breeding method for improving the cotton fiber strength by using a chr.7 single QTL segment substitution line, including the steps of: (1) using Lumianyan 22 as a female parent and Luyuan 343 as a male parent to construct a recombinant inbred line (RIL) $F_8$, utilizing this population to detect one major-effect QTL associated with fiber strength on a chr.7 chromosome, selecting an individual plant carrying the target chr.7 single QTL segment to continuously back cross with the Lumianyan 22 for 3-5 times, and using an SSR molecular marker to screen back-crossed offsprings for obtaining a chr.7 single QTL segment substitution line with high fiber strength; (2) using the chr.7 single QTL segment substitution line obtained in step (1) as a non-recurrent parent to cross with a recurrent parent to obtain an $F_1$ generation, the recurrent parent being a parent having a fiber quality to be improved; (3) back crossing the $F_1$ generation obtained in step (2) with the recurrent parent to obtain a $BC_1F_1$ generation; (4) using the SSR molecular marker to screen plants of the $BC_1F_1$ generation for plants carrying the target chr.7 single QTL segment, and back crossing the screened plants with the recurrent parent for 2-4 times to obtain a $BC_nF_1$ generation; and (5) using the SSR molecular marker to screen plants of the $BC_nF_1$ generation for plants carrying the target chr.7 single QTL segment, and selfing the screened plants for 1-3 times to obtain a bred line BCnFm having high cotton fiber strength. The primer pair used for SSR molecular marker screening includes DPL0852, DPL0757 and DC40182; and the sequences are Seq ID Nos. 1-6, respectively.

In embodiments of the present invention, the chr.7 single QTL segment substitution line having the high cotton fiber strength serves as a non-recurrent parent, thereby providing the recurrent parent with a gene resource having excellent fiber quality. In one example, the chr.7 single QTL segment substitution line having the high cotton fiber strength is obtained by using Lumianyan 22 (♀) and Luyuan 343 (♂) as parents to construct a recombinant inbred line (RIL) $F_8$, and continuously back crossing an individual plant of the RIL $F_8$ with the Lumianyan 22 for 4-6 times. The Lumianyan 22 described in the present invention is a transgenic insect-resistant cotton variety with excellent comprehensive traits and wide adaptability cultivated by Shandong Cotton Research Center, which has a high lint percentage; and Luyuan 343 is a new upland-type long-staple cotton line introgressed by the excellent fiber quality genetic resources from Sea-Island cotton, which has superior fiber quality. In the present invention, Lumianyan 22 (♀) having a high lint percentage and Luyuan 343 (♂) having an excellent fiber quality are used as parents to construct a recombinant inbred line $F_8$. There are total 358 families in the recombined inbred line $F_8$. In the present invention, preferably one individual plant with excellent traits is selected from the 358 families, and the individual plant with excellent traits has a fiber length (FL) of 35.47 mm, a fiber strength (FS) of 39.3 cN/tex, and a fiber micronaire (FM) of 4.01.

In embodiments of the present invention, the individual plant with excellent traits is continuously back-crossed with the recurrent parent Lumianyan 22 for 3-5 times, preferably 4 times, and in the present invention preferably each generation during the back-cross process is selected as assisted by the molecular marker, to obtain the chr.7 single QTL segment substitution line having the high cotton fiber strength (SL7). The molecular marker is preferably an SSR molecular marker, the primer pair of the SSR molecular marker includes DPL0852, DPL0757, and DC40182; and the sequences are Seq ID Nos. 1-6.

These SSR molecular marker primers are used to amplify DNA of the whole genome of the plant of each generation. For example, a preferred PCR amplification system is 10 μl, and specifically includes: ultrapure water (ddH$_2$O) of 4.7 μl, a template DNA of 1.0 μl, a 10× Buffer of 1.0 μl, 2.5 mM MgCl$_2$ of 1.0 μl, 10 mM dNTPs of 0.2 μl, a forward primer of 1.0 μl and a reverse primer of 1.0 μl for each molecular marker at a concentration of 10 μM, and a Taq DNA polymerase of 0.1 μl. The SSR-molecular-marker PCR amplification reaction procedure described in the present invention is preferably: preheating at 95° C. for 5 min, denaturalizing at 94° C. for 45 s, annealing at 52-57° C. for 45 s, extending at 72° C. for 1 min; circulating for 30 times, and extending at 72° C. for 10 min.

In the present invention, after the PCR amplification reaction is completed, the amplification product is preferably stored at 4° C. Then an 8% non-denaturing polyacrylamide (PAGE) gel electrophoresis is utilized to detect the product band, the product band is subjected to silver staining and color development to observe the results. If the amplification results only include three corresponding molecular marker bands amplified from the primer pairs DPL0852, DPL0757 and DC40182, i.e., the plants carrying the chr.7 single QTL segment, subsequent experiments can be performed.

In the present invention, the chr.7 single QTL segment substitution line having the high cotton fiber strength has a fiber length of 30-31.1 mm, and fiber strength of 31-33.3 cN/tex; and the fiber length and fiber strength of the chr.7 single QTL segment substitution line having the high cotton fiber strength (SL7) are significantly different from those of the parent Lumianyan 22.

In embodiments of the present invention, after the chr.7 single QTL segment substitution line having the high cotton fiber strength is obtained, the chr.7 single QTL segment substitution line having the high cotton fiber strength is used as a non-recurrent parent to cross with the recurrent parent (♀) so as to obtain the $F_1$ generation. The non-recurrent parent described in the present invention is a parent having a fiber quality to be improved; and preferably is a variety having a high yield, a high lint percentage (greater than 43%), and a general fiber strength; and the recurrent parent described in the specific implementation of the present invention can be Lumianyan 29, Lu 7619, Lu 6269, Ji 958, Lumianyan 36, Lumianyan 37, Luan S3586, Lumian 301, Lumian 319, or other conventional upland cotton varieties that meet the requirements. The crossing described in the present invention can be performed by using a conventional crossing method in the art, without any other special requirements.

Preferably, after the $F_1$ generation is obtained, screening of the plants of the $F_1$ generation is conducted with the SSR molecular marker. That is, in the $F_1$ generation, the DNA of the plants is extracted by applying a CTAB method and is amplified through PCR by using the molecular marker primer pairs DPL0852, DPL0757 and DC40182 on the chr.7 single QTL segment substitution line SL7 having the high cotton fiber strength. The specific PCR system and procedure are conducted by using the system and procedure described in the above technical solution and will not be described in detail any more herein; and if the amplification results only include three corresponding molecular marker bands, i.e., the plants carrying the chr.7 single QTL segment, subsequent experiments can be performed. In the present invention, each of individual plants of the F1 generation contains a donor segment.

In embodiments of the present invention, after the $F_1$ generation is obtained, the obtained F1 generation is back-crossed with the recurrent parent to obtain the $BC_1F_1$ generation. The back-crossing described in the present invention can be performed by using a conventional back-crossing method in the field, without other special requirements.

In some embodiments, after the $BC_1F_1$ generation is obtained, the $BC_1F_1$ generation is planted, and is screened by adopting the SSR molecular marker for plants carrying the chr.7 single QTL segment. The SSR-molecular-marker screening method is the same as that described above, and will not be described in detail any more herein.

After the plants of $BC_1F_1$ generation carrying the chr.7 single QTL segment are obtained, the plants of $BC_1F_1$ generation carrying the chr.7 single QTL segment are back-crossed with the recurrent parent for 2-4 times to obtain the $BC_1F_1$ generation. In the present invention, the number of times of back-cross is preferably 3; the $BC_3F_1$ generation is obtained after the 3 back-crosses; and in the present invention, each back-crossed generation is preferably screened by means of the SSR molecular marker to obtain a plant carrying the chr.7 single QTL segment.

After the $BC_1F_1$ generation is obtained, a plant carrying the chr.7 single QTL segment is screened out from the plants of the $BC_1F_1$ generation, and then the plant carrying the chr.7 single QTL segment is selfed for 1-3 times to obtain a bred line $BC_nF_m$ having the high cotton fiber strength. In the present invention, the method for screening the plant carrying the chr.7 single QTL segment is the SSR molecular marker, which will not be described in detail any more herein. In the present invention, after the plant of the $BC_1F_1$ generation carrying the chr.7 single QTL segment is obtained, the obtained plant of the $BC_1F_1$ generation carrying the chr.7 single QTL segment is selfed for 1-3 times; and preferably for two times. In such embodiments, $BC_3F_1$ is selfed for two times to obtain a bred line $BC_3F_3$ having high cotton fiber strength. In the selfing process, preferably the SSR molecular marker is used to screen out the plant carrying the chr.7 single QTL segment for the next selfing; and a bred line having high cotton fiber strength is obtained after the selfing is completed.

The bred line having the high cotton fiber strength obtained in the present invention can be planted in different geographical environments, and the excellent fiber quality of the bred line having the high cotton fiber strength can be stably inherited.

The molecular breeding method for improving the cotton fiber strength by using the chr.7 single QTL segment substitution line provided by the present invention will be described in detail in connection with specific embodiments hereafter, but the embodiments should not be construed as limiting the claimed scope of the present invention.

Embodiment 1

The construction of the chr.7 single QTL segment substitution line includes: the Lumianyan 22 described in the present invention is a transgenic insect-resistant cotton variety with excellent comprehensive traits and wide adaptability cultivated by Shandong Cotton Research Center, which has a high lint percentage; and Luyuan 343 is a new upland-type long-staple cotton variety introgressed by the excellent fiber germplasm of a sea island cotton, which has great fiber quality. The Lumianyan 22 (♀) having the high lint percentage and the Luyuan 343 (♂) having the excellent fiber germplasm were used as parents to construct a recombination inbred line F8 including 358 families, and an individual plant with good traits (with an FL of 35.47 mm, an FS of 39.3 cN/tex-1, and an FM of 4.01) was selected and then continuously back-crossed with the recurrent parent (Lumianyan 22), and the back-crossed offsprings were screened as assisted by the molecular marker to obtain a single segment substitution line (SL7) with high fiber strength. The fiber length was 30-31.1 mm, and the fiber strength was 31-33.3 cN/tex, which were significantly different from those of the recurrent parent.

The selection of recurrent parents with different genetic backgrounds includes: the principle for selecting the parents with different genetic backgrounds was a high yield (increased by 10% as compared with a control), a high lint percentage (greater than 43%), and general fiber quality. 4 national approved varieties were selected at Yellow River basin, such as: Lumianyan 29, Lu 7619, Lu 6269, and Ji 958; 2 approved varieties at Shandong Province, such as Lumianyan 36, Lumianyan 37; and 3 high-yield new varieties created by the present research group, such as Lu 53586, Lumian 301, and Lumian 319.

The chr.7 single QTL segment substitution line was used as the non-recurrent parent (♂) to cross with the recurrent parent (♀) to obtain an F1 generation; and the fiber strength was evaluated at the $F_1$ generation, with the results shown in FIG. 1: the $F_1$ generation had its fiber strength improved in different genetic backgrounds, P2 and P9 had different fiber strength at a level of 5%, and P1, P3, P4, P5, P6, P7 and P8 had significantly improved fiber strength at a level of 1%.

Molecular Marker-Assisted Selection

In the winter of 2014, $F_1$ and its respective parents were planted in Sanya, Hainan. Three replicates were planted in each combination, with 15-20 plants per row. In the squaring stage, individual plants were sampled from the whole row, placed into a 2.0 ml centrifuge tube, added with 600 μl of a freshly prepared extracting solution, and placed into a tissue mill for grinding. The DNA was extracted using the CTAB method and amplified through PCR by using the molecular marker on the single segment substitution line (SL7) (Table 1). The PCR reaction system was 10 μl, including ultrapure water (ddH$_2$O) of 4.7 μl, a template DNA of 1.0 μl, a 10× Buffer of 1.0 μl, 2.5 mM MgCl$_2$ of 1.0 μl, 10 mM dNTPs of 0.2 µl, a forward primer of 1.0 µl and a reverse primer of 1.0 µl for each molecular marker at a concentration of 10 µM, and a Taq DNA polymerase of 0.1 µl. The SSR amplification reaction procedure includes: preheating at 95° C. for 5 min, denaturing at 94° C. for 45 s, annealing at 52-57° C. for 45 s, extending at 72° C. for 1 min; cycling for 30 times, and extending at 72° C. for 10 min; and the amplification product was stored at 4° C. until removed. The removed amplification product was subjected to an 8% non-denaturing polyacrylamide (PAGE) gel electrophoresis, silver staining, and color development. The silver staining and color development process included: silver staining with 0.1% AgNO3 for 12-15 min, developing a color with 2% NaOH+1% formaldehyde for 5-10 min, rinsing with distilled water for 2-3 times, and recording the results. An individual plant containing three molecular markers was selected and then crossed with the corresponding recurrent parent to obtain $BC_1F_1$.

In the summer of 2017, the $F_1$, the $BC_3F_3$ and their respective parents were planted at the Linqing Experimental Station of the Shandong Cotton Research Center and the Baibi Experimental Station of the Institute of Cotton Research (ICR) of the Chinese Academy of Agricultural Sciences (CAAS). Three replicates were planted in each combination, with 15-20 plants per row. The $BC_3F_3$ generation also had its fiber strength improved under different genetic backgrounds, and as shown in FIG. 2, P1 and P2 had different fiber strength at a level of 5%, and P3, P5, P7 and P8 had significantly improved fiber strength at a level of 1%.

In the summer of 2017, $F_1$, $BC_3F_3$ and their respective parents were planted at the Linqing Experimental Station of the Shandong Cotton Research Center and the Baibi Experimental Station of the Institute of Cotton Research (ICR) of the Chinese Academy of Agricultural Sciences (CAAS). Three replicates were planted in each combination, with 15-20 plants per row. 20 bolls were harvested from each row,

TABLE 1

SSR Molecular Marker of Single segment substitution line (SL7)

| Name of Primer | Sequence of Forward Primer | Sequence of Reverse Primer |
| --- | --- | --- |
| DPL0852 | gttccaaatcaatctcgtgt (Seq. ID No. 1) | ggctgttacagatcaaactccc (Seq. ID No. 2) |
| DPL0757 | ccctacaacagtttgataccatga (Seq. ID No. 3) | attgagggtattgctatacatcgg (Seq. ID No. 4) |
| DC40182 | aaaatactaaagtcgatagaattgc (Seq. ID No. 5) | accgttccaaatagggtc (Seq. ID No. 6) |

In the summer of 2015, $BC_1F_1$ and its respective parents were planted at the Linqing Experimental Station of Shandong Cotton Research Center, with 15-20 plants per row. DNA was extracted from each plant sample and amplified using a molecular marker on the single segment substitution line (SL7) (Table 1). The genotype of the $BC_1F_1$ was determined, an individual plant containing three molecular markers was selected to back-cross with the corresponding recurrent parent to obtain $BC_2F_1$, and the seeds were harvested per individual plant.

In the winter of 2015, the $BC_2F_1$ and its respective parents were planted in Sanya, Hainan. The above described steps were repeated to obtain $BC_3F_1$, and the seeds were harvested per individual plant.

In the summer of 2016, the $BC_3F_1$ and its respective parents were planted at the Linqing Experimental Station of Shandong Cotton Research Center, with 15-20 plants per row. DNA was extracted from each plant sample and amplified using the molecular marker on the single segment substitution line (SL7) (Table 1). The genotype of the $BC_3F_1$ was determined, an individual plant containing three molecular markers was selected to be selfed to obtain $BC_3F_2$, and a mixture of seeds was harvested per homozygous individual plant.

In the winter of 2016, $BC_3F_2$ and its respective parents were planted in Sanya, Hainan, with 15-20 plants per row. DNA was extracted from each plant sample and amplified using the molecular marker on the single fragment substitution line (SL7) (Table 1). The genotype of the $BC_3F_2$ was determined, an individual plant containing three molecular markers was selected to selfing to obtain $BC_3F_3$, and a mixture of seeds was harvested per homozygous individual plant.

and 20 g lint cotton was sent to the Fiber Testing Center of the Ministry of Agriculture (the ICR of CAAS) to detect the fiber strength, and the tested results were shown in Table 2.

TABLE 2

Tested Fiber Strength Results of $F_1$ and $BC_3F_3$ Generations (unit: $cN \cdot tex^{-1}$)

|  | P | $F_1$ | $BC_3F_3$ |
| --- | --- | --- | --- |
| P1 | 30 | 32.5 | 31.9 |
|  | 30.3 | 32 | 32.4 |
|  | 30.3 | 32.3 | 31.6 |
|  | 30.6 | 32.5 | 32.1 |
| Mean Value | 30.3 | 32.325 | 32 |
| Standard Deviation | 0.244949 | 0.236291 | 0.33665 |
| P2 | 29.6 | 31.4 | 31.6 |
|  | 29.4 | 31.3 | 31.1 |
|  | 29.8 | 31.2 | 30.9 |
|  | 29.2 | 31.8 | 31.2 |
| Mean Value | 29.5 | 31.425 | 31.2 |
| Standard Deviation | 0.258199 | 0.262996 | 0.294392 |
| P3 | 26.2 | 31.2 | 29.5 |
|  | 25.9 | 31.3 | 29.9 |
|  | 26.1 | 31.3 | 30.3 |
|  | 26.2 | 31.4 | 29.9 |
| Mean Value | 26.1 | 31.3 | 29.9 |
| Standard Deviation | 0.141421 | 0.08165 | 0.326599 |
| P4 | 29 | 32.4 | 29.3 |
|  | 28.6 | 32.2 | 29.8 |
|  | 28.7 | 31.8 | 29.2 |
|  | 28.5 | 32 | 30.1 |
| Mean Value | 28.7 | 32.1 | 29.6 |
| Standard Deviation | 0.216025 | 0.258199 | 0.424264 |
|  | 27.6 | 31.6 | 29.1 |
| P5 | 27.5 | 29.1 | 30.1 |
|  | 27.9 | 30.6 | 29.5 |
|  | 27.4 | 32.3 | 29.7 |

TABLE 2-continued

Tested Fiber Strength Results of $F_1$ and $BC_3F_3$ Generations (unit: $cN \cdot tex^{-1}$)

|  | P | $F_1$ | $BC_3F_3$ |
|---|---|---|---|
| Mean Value | 27.6 | 30.9 | 29.6 |
| Standard Deviation | 0.258199 | 0.262996 | 0.294392 |
| P6 | 26.1 | 30.3 | 26.8 |
|  | 26.9 | 30.7 | 27.4 |
|  | 26.6 | 30.6 | 26.9 |
|  | 26.8 | 31.1 | 26.9 |
| Mean Value | 26.6 | 30.675 | 27 |
| Standard Deviation | 0.355903 | 0.330404 | 0.270801 |
| P7 | 25.5 | 30.5 | 30.3 |
|  | 25.3 | 30.8 | 29.5 |
|  | 25.1 | 30.4 | 29.1 |
|  | 25.3 | 30.6 | 29.9 |
| Mean Value | 25.3 | 30.575 | 29.7 |
| Standard Deviation | 0.163299 | 0.170783 | 0.516398 |
| P8 | 27.1 | 32.3 | 29.6 |
|  | 27.6 | 31.8 | 29.9 |
|  | 26.6 | 32.7 | 30.2 |
|  | 26.7 | 32.3 | 29.5 |
| Mean Value | 27 | 32.275 | 29.8 |
| Standard Deviation | 0.454606 | 0.368556 | 0.316228 |
| P9 | 29.2 | 31.2 | 29.9 |
|  | 29.1 | 31.4 | 30 |
|  | 28.7 | 31.3 | 30.2 |
|  | 29 | 31.3 | 30.3 |
| Mean Value | 29 | 31.3 | 30.1 |
| Standard Deviation | 0.216025 | 0.08165 | 0.182574 |
| SL7 | 32 |  |  |
|  | 31.9 |  |  |
|  | 32.1 |  |  |
|  | 31.5 |  |  |
| Mean Value | 31.875 |  |  |
| Standard Deviation | 0.262996 |  |  |

As can be seen from the above embodiments, in the cotton molecular breeding method using the chr.7 single QTL segment substitution line having the high cotton fiber strength as provided by the present invention, by using the chr.7 single QTL segment substitution line having the high cotton fiber strength to continuously back-cross with different cotton varieties/strains having a high yield but undesirable fiber quality, the segment substitution line is introduced into upland cotton with different genetic backgrounds. The target traits are selected in connection with the assistance of the molecular marker and are evaluated in $F_1$ and $BC_3F_3$ generations. Therefore, this method can systematically and effectively improve the cotton fiber strength and can quickly and efficiently develop a new cotton variety/line which is excellent (having high fiber strength).

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A molecular breeding method for improving cotton fiber strength by using a chr.7 single QTL segment substitution line, the method comprising:
   (1) constructing a recombinant inbred line $F_8$ from Lumianyan 22 as a female parent and Luyuan 343 as a male parent, detecting one major-effect QTL associated with fiber strength on a Chr.7 chromosome from the population of the recombinant inbred line $F_8$, selecting an individual plant carrying the target Chr.7 single QTL fragment to continuously back cross with the Lumianyan 22 for 3-5 times, and screening back-crossed offspring with SSR molecular markers for obtaining a chr.7 single QTL segment substitution line with high fiber strength;
   (2) crossing the chr.7 single QTL segment substitution line obtained in step (1) as a non-recurrent parent with a recurrent parent to obtain an $F_1$ generation, the recurrent parent being a parent having a fiber strength to be improved, and the recurrent parent selected from Lumianyan 29, Lu 7619, Lu 6269, Ji 958, Lumianyan 36, Lumianyan 37, Lu S3586, Lumian 301, and Lumian 319;
   (3) back-crossing the $F_1$ generation obtained in step (2) with the recurrent parent to obtain a $BC_1F_1$ generation;
   (4) screening plants of the $BC_1F_1$ generation with SSR molecular markers for plants carrying the target chr.7 single QTL segment, and back crossing the screened plants with the recurrent parent for 2-4 times to obtain a $BC_nF_1$ generation, wherein n is a number of times of back-cross; and
   (5) screening plants of the $BC_nF_1$ generation with SSR molecular markers for plants carrying the target chr.7 single QTL segment, and selfing the screened plants for 1-3 times to obtain a bred line $BC_nF_m$ having high cotton fiber strength;
   wherein the SSR molecular markers are used after each time of selfing to screen out a plant carrying the chr.7 single QTL segment for a next selfing; and
   wherein the primer pair used for SSR molecular marker screening comprises a DPL0852 primer pair, a DPL0757 primer pair and a DC40182 primer pair; and the sequences are SEQ. ID. NOs. 1-6 respectively, said SEQ. ID NOs. referencing the primer pairs of the SSR molecular markers used for screening.

2. The method of claim 1, wherein the chr.7 single QTL segment substitution line has a fiber length of 30-31.1 mm and fiber strength of 31-33.3 cN/tex.

3. The method of claim 1, wherein the number of times of back-cross in step (4) is 3.

4. The method of claim 1, wherein a number of times of selfing in step (5) is 2.

* * * * *